United States Patent
Laswell et al.

(10) Patent No.: US 7,453,266 B2
(45) Date of Patent: Nov. 18, 2008

(54) ELECTRONIC HUMIDITY CHAMBER FOR VAPOR DESORPTION TO DETERMINE HIGH CAPILLARY PRESSURES

(76) Inventors: Patrick M. Laswell, 6211 Elmgrove Rd., Spring, TX (US) 77389; Kent E. Newsham, 11 Bayginger Pl., The Woodlands, TX (US) 77381

(*) Notice: Subject to any disclaimer, the term of this patent is extended or adjusted under 35 U.S.C. 154(b) by 17 days.

(21) Appl. No.: 11/903,975

(22) Filed: Sep. 25, 2007

(65) Prior Publication Data
US 2008/0024135 A1 Jan. 31, 2008

Related U.S. Application Data

(62) Division of application No. 10/956,809, filed on Oct. 1, 2004, now Pat. No. 7,171,843, and a division of application No. 11/645,460, filed on Dec. 26, 2006, now Pat. No. 7,406,857.

(51) Int. Cl.
G01V 3/00 (2006.01)
E21B 49/02 (2006.01)
G01N 15/08 (2006.01)

(52) U.S. Cl. .......... 324/376; 73/38; 73/152.09
(58) Field of Classification Search .......... 73/38, 73/152.09; 324/376
See application file for complete search history.

(56) References Cited

U.S. PATENT DOCUMENTS

| | | | |
|---|---|---|---|
| 4,546,318 A * | 10/1985 | Bowden | 324/376 |
| 4,625,544 A | 12/1986 | Hi-Hwa Yuan et al. | 73/38 |
| 4,752,882 A * | 6/1988 | Givens | 702/13 |
| 5,069,065 A | 12/1991 | Sprunt et al. | 73/152.09 |
| 5,164,672 A * | 11/1992 | Gilliland et al. | 324/376 |
| 5,209,104 A * | 5/1993 | Collins et al. | 73/38 |
| 5,425,265 A | 6/1995 | Jaisinghani | 73/38 |
| 5,493,226 A | 2/1996 | Honarpour et al. | 324/376 |
| 6,021,662 A | 2/2000 | Moulu et al. | 73/38 |
| 6,229,312 B1 * | 5/2001 | Fleury et al. | 324/376 |
| 7,072,809 B2 | 7/2006 | Egermann et al. | 703/2 |
| 7,171,843 B2 * | 2/2007 | Laswell et al. | 73/38 |
| 7,221,165 B2 * | 5/2007 | Fleury | 324/376 |

OTHER PUBLICATIONS

J. C. Melrose, Use of Water Vapor Desorption Data in the Determination of Capillary Pressures, Society of Petroleum Engineers, 1987, pp. 465-475.

* cited by examiner

*Primary Examiner*—Hezron E. Williams
*Assistant Examiner*—John Fitzgerald
(74) *Attorney, Agent, or Firm*—G. Alan Witte

(57) ABSTRACT

The present invention relates to the use of an electronically controlled humidity chamber with temperature controls: to determine, by vapor desorption, high capillary pressures of core samples; to produce core samples with a high capillary pressure for testing electrical properties; and, using a curve of high capillary pressures from vapor desorption data, to transform a curve of high capillary pressures determined from high pressure mercury injection.

2 Claims, 3 Drawing Sheets

ELECTRONIC HUMIDITY CHAMBER FOR VAPOR DESORPTION TO DETERMINE HIGH CAPILLARY PRESSURES

RELATED APPLICATIONS

The present application is a second Divisional of U.S. patent application Ser. No. 10/956,809, filed Oct. 1, 2004, entitled "ELECTRONIC HUMIDITY CHAMBER FOR VAPOR DESORPTION TO DETERMINE HIGH CAPILLARY PRESSURES," now, U.S. Pat. No. 7,171,843. The first Divisional is U.S. patent application Ser. No. 11/645,460, filed Dec. 26, 2006, now, U.S. Pat. No. 7,406,857.

BACKGROUND OF THE INVENTION

1. Field of the Invention

This present invention relates to the use of an electronically controlled humidity chamber with temperature controls to collect vapor desorption data which is used to calculate the capillary pressure of a core sample. In another aspect of the present invention, a core sample with a high capillary pressure is produced and at least one electrical property is determined. In another aspect of the present invention, the capillary pressures determined according to the present invention are used to transform capillary pressures determined from the high pressure mercury injection method.

2. Description of the Related Art

Knowledge of capillary pressure or each specific rock/oil/water combination present in reservoir rocks is highly important for predicting potential hydrocarbon in place within a reservoir. Capillary pressure data is a measure of the interaction between fluids and the rock pore surface. The strength of capillary interaction varies with the fluid saturations, the interfacial tension between the fluids, the pore structure, and the wettability of the pore surfaces.

Capillary pressure measurements also provide basic descriptions of the reservoir rock, fluids and rock-fluid behavior. Capillary pressure data may be used to: estimate pore throat size distribution to classify hydraulic rock types; determine initial water saturation conditions; estimate water saturation, permeability, porosity, and height above free water level for reserve estimates; estimate absolute permeability; estimate seal capacity of the sealing facies; and estimate capillary pressure water saturation profiles.

Several techniques have been developed for measuring capillary pressures of core samples, including porous plate, centrifuge and mercury injection. As known by one of skill in the art, the porous plate and centrifuge methods have the advantage of being able to use reservoir fluids during the capillary pressure measurements; however, limitations on the maximum achievable capillary pressure preclude application in situations where high capillary pressure exists, such as tight gas sands. The porous plate and centrifuge methods are generally limited to capillary pressures up to about 1000 psi.

High-pressure mercury-injection can reach the necessary pressures, typically 5000 to 10,000 psi, but the use of non-reservoir fluids to compute capillary pressures produces inaccurate results and transformation is required to correct the capillary pressure data. The inaccurate results are believed to be due to the lack of a true wetting phase during testing. The test is performed on dry samples using mercury as the non-wetting phase fluid and assuming air is the wetting liquid. This requires conversion to reservoir conditions using contact angle and surface tension inputs. Additionally, the oil and gas industry lacks a consensus of standards for correcting system compressibility at high pressures resulting in water saturation/capillary pressure distribution measurement uncertainties. Finally, use of the contact angle and surface tension scaling parameters are generally not appropriate for rocks with ultra-low water saturations and high capillary pressures or rocks common to tight gas sand reservoirs.

It is also known that the vapor desorption method can be used to calculate capillary pressures. While the vapor desorption method produces accurate results at moderately high capillary pressures and moderately low water saturations, the vapor desorption measurement precision decreases at very high relative humidity (>95%) which limits the lower limit of capillary pressure to a range of approximately 1000 psi. Thus, a disadvantage of the vapor desorption technique is the inability to measure capillary pressures at high water saturations.

For the vapor desorption method, it is known that the Kelvin relationship: $Pc=\ln(RH/100)RT/Vm$, (where: Pc is the capillary pressure, psi; RH is the relative humidity; R is the universal gas constant, 8.314 J/Mol K; T is the absolute temperature, degrees Kelvin; and Vm is the molar volume of water) can be used to compute air/brine capillary pressures for core samples. (The Kelvin relationship is known to those of skill in the art.) This is detailed in SPE Paper No. 16286, "Use of Water Vapor Desorption Data in the Determination of Capillary Pressures". Experimentally, the core samples are allowed to reach equilibrium in a constant vapor pressure environment. As discussed in the paper, a known way to establish the constant vapor pressure environment is to use saturated solutions of salts such as $BaCl_2$, $KNO_3$, and $K_2SO_4$. Using the vapor pressure data for these solutions, the Kelvin capillary pressures are calculated for a range of NaCl brine compositions and a range of temperatures. The lowest humidity level shown in the paper is 0.8987 produced by a saturated solution of $BaCl_2$ at 30° C. Applicants are not aware of salt solutions that will produce practical humidity levels below this 0.8987 level. The paper discusses the use of salt solutions to calculate capillary pressures as high as 4000 psi.

Electrical properties such as formation factor and resistivity index are often calculated at a number of varying water saturations or capillary pressures. However, because the porous plate and centrifuge methods are limited on the maximum capillary pressure, the calculation of these electrical properties has been limited to high water saturations and low capillary pressures.

Thus, there are a number of shortcomings with the prior art, including: the inability to accurately determine high capillary pressures; the inability to produce core samples having low water saturation and high capillary pressure for measurement of electrical properties; and the inability to obtain accurate capillary pressures using the high-pressure mercury injection method.

SUMMARY OF THE INVENTION

Accordingly, a need has arisen for a method of determining high capillary pressure, e.g., in excess of 4,200 psi and the corresponding low water saturations, e.g., approximately 5%. A further need exists for determining electrical properties of core samples at high capillary pressures. A further need exists for a method of transforming the capillary pressures determined from high-pressure mercury injection, particularly at high capillary pressures.

In accordance with present invention, an electronically controlled humidity chamber with temperature controls is used to control humidity in a method using vapor desorption to determine capillary pressures of a core sample or to produce high capillary pressure within a core sample.

Accordingly, an object of the present invention is to use an electronically controlled humidity chamber with temperature controls to provide a method of using vapor desorption to measure high capillary pressures, e.g., in excess of 4,200 psi and at low water saturations, e.g., below 5%.

A further object of the present invention is to use an electronically controlled humidity chamber with temperature controls to produce core samples having low water saturation and high capillary pressures. The electrical properties of these core samples may then be determined.

A still further object of present invention is to use an electronically controlled humidity chamber with temperature controls to collect vapor desorption data to determine the capillary pressures of core samples which can then be used to transform the capillary pressure data determined according to the high-pressure mercury injection method.

BRIEF DESCRIPTION OF THE DRAWINGS

A better understanding of the invention can be obtained when the detailed description of exemplary embodiments set forth below is considered in conjunction with the attached drawings in which.

DETAILED DESCRIPTION OF THE EXEMPLARY EMBODIMENTS

Figure 1:
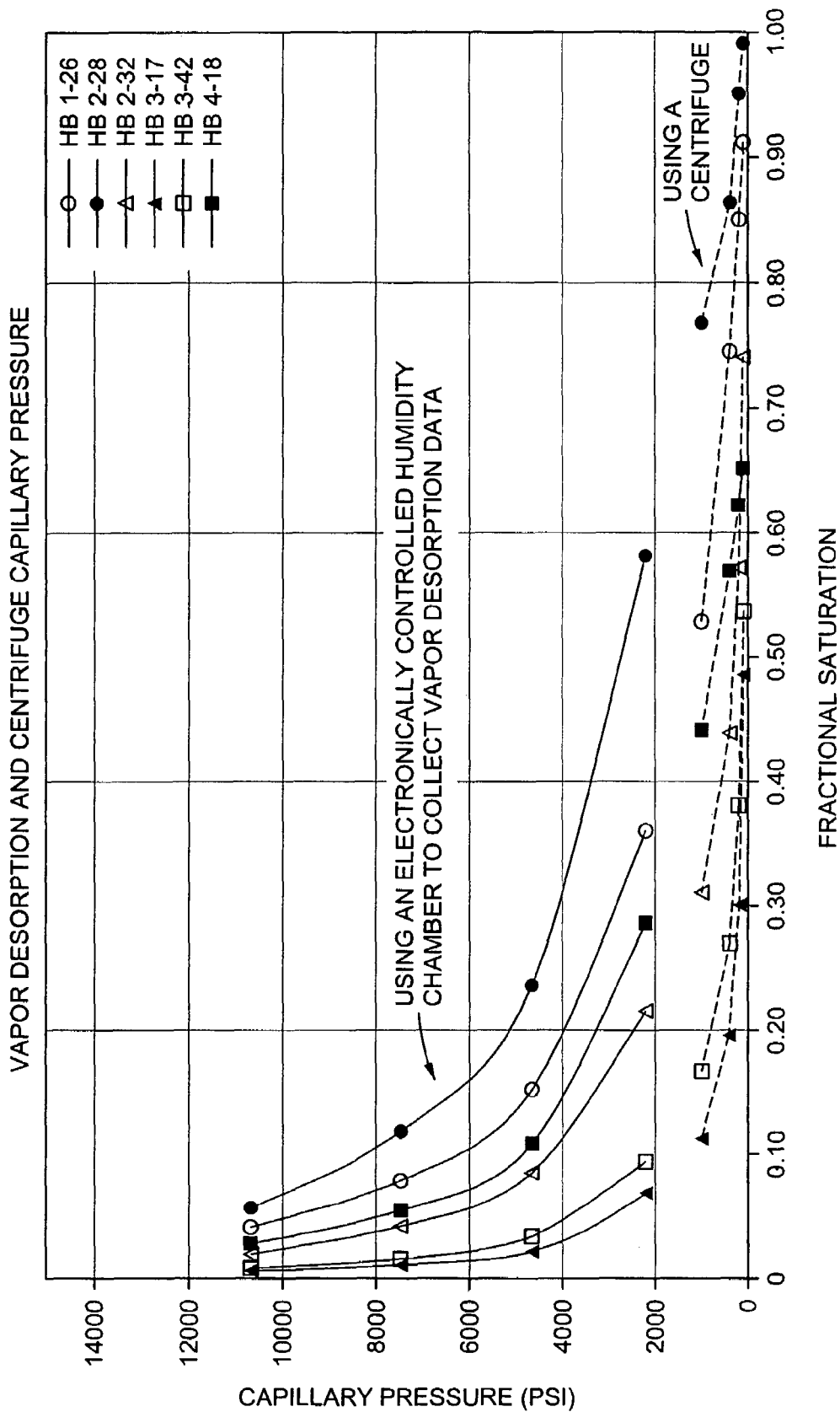
FIG. 1 is a graphical presentation of capillary pressures from Experiment 1 reported herein.

The present invention relates to a method of using an electronically controlled humidity chamber with temperature controls to collect vapor desorption data which is used to calculate the capillary pressure of a core sample. The electronically controlled humidity chamber has an electronic relative humidity sensor and water is sprayed into the chamber to maintain the humidity at the desired level. The humidity chamber controls both humidity and temperature electronically. Humidity is maintained within 1 percentage unit and temperature is controlled within 1 degree. The humidity chamber can be set at a relative humidity (RH) from 90% (which corresponds to a capillary pressure of approximately 2,200 psi) to a RH of 55% (which corresponds to a capillary pressure of approximately 12,500-14,000 psi). In fact, the humidity chamber can be controlled to a RH of approximately 25% (which corresponds to a capillary pressure of approximately 30,000 psi). The temperature range can be controlled between 25° C.-60° C.

Tight gas sands constitute a significant percentage of the U.S. natural gas base and offer tremendous potential for future reserve growth and production. Tight gas sands often exhibit unique gas storage and producing characteristics. Many tight gas sands are also characterized by very low connate water saturations and associated high capillary pressures. Consequently, effective exploitation of these resources requires accurate descriptions of key reservoir parameters, particularly capillary pressures, to quantify the vertical water saturation distribution and resource-in-place. As noted above, the prior art does not provide a method for accurately determining the high capillary pressures associated with these low water saturations.

In accordance with the present invention, a method for determining the capillary pressure of a core sample most preferably at or above about 4,200 psi (also preferably at or above 5,000 psi) (further preferably at or above about 6,000 psi) is provided, the method comprising the steps of: initially desaturating the core sample at a capillary pressure of 1000 psi, placing the core sample in an electronically controlled humidity chamber with temperature controls, setting a humidity level in the humidity chamber at about 80 percent or lower, periodically weighing the core sample to determine when equilibrium water saturation is achieved at the humidity level, and calculating the capillary pressure at 2000 psi. The vapor desorption process is continued in a step-wise manner at decreasing relative humidity levels yielding increasing capillary pressures to an approximate maximum capillary pressure of approximately 14,000 psi.

As is known to one of skills in the art, electrical properties of core samples, e.g., formation factor, resistivity index, cementation exponent and saturation exponent, are important in determining the water or oil and/or gas reserves in place. Prior to the present invention, there was no known way to produce core samples having high capillary pressures (at or above 4200 psi) and low water saturations (below about 5%) on which electrical properties could be tested. Vapor desorption using salt solutions is limited to a capillary pressure of 4000 psi. The centrifuge and porous plate methods are limited to capillary pressures of about 1000 psi. While high-pressure mercury injection is capable of measuring capillary pressures up to 60,000 psi, it is a destructive testing method and the resulting core samples are not suitable for testing electrical properties.

In accordance with the present intention, a method for determining an electrical property of a core sample having a capillary pressure above about 4,200 psi is provided, comprising the steps: Initially determining electrical properties using conventional methods to a maximum capillary pressure of 1000 psi. The desaturation process is then continued by placing the core sample in an electronically controlled humidity chamber with temperature controls, setting a humidity level in the humidity chamber at about 80%, periodically weighing the core sample to determine when equilibrium water saturation is achieved at the humidity level, calculating the capillary pressure at or above about 4,200 psi, and measuring an electrical property of the core sample at that saturation level. The desaturation process is then continued at a lower relative humidity percentages (higher capillary pressures) in the humidity chamber and the electrical properties determined at each stability saturation point.

The determination of high-pressure mercury injection capillary pressures (MICP) involves injecting or forcing mercury into an evacuated core sample in a step-wise manner from vacuum to 60000 psi air-mercury. The volume of mercury injected at each pressure determines the non-wetting (i.e., mercury) saturation. Then, as known by one of skill in the art, the corresponding wetting phase capillary pressure is calculated at each mercury injection pressure.

In accordance with the present invention, a method for building a transform between wetting fluid saturations and those non-wetting saturations determined using high pressure mercury injection is provided, comprising the steps of: in a step wise fashion, injecting mercury into an evacuated core sample at a number of pressures, measuring the volume of mercury injected at each pressure, calculating the capillary pressure by high-pressure mercury injection at each pressure, in a step wise fashion, using an electronically controlled humidity chamber with temperature controls to collect vapor desorption data, using the vapor desorption data, calculating a step wise series of capillary pressures at or above about 4,200 psi, using the capillary pressures calculated from the vapor desorption data, transforming the capillary pressure data determined by high pressure mercury injection. The formula for transforming the high-pressure mercury injection capillary pressure is:

$$P_{cAW} = P_{cAM}\left(\frac{2\sigma_{AW}\cos\theta_{AW}}{2\sigma_{AM}\cos\theta_{AM}}\right)$$

(where: $P_{cAW}$=pseudo air-water capillary pressure, psi; $P_{cAM}$=air-mercury capillary pressure, psi; $\sigma_{AW}$=air-water surface tension; $\sigma_{AM}$=air-mercury surface tension; $\cos\theta_{AW}$=air-water contact angle; $\cos\theta_{AM}$=air-mercury contact angle) further comprising the steps of: graphing the capillary pressures calculated from the vapor desorption data to produce a vapor desorption curve; graphing the capillary pressures determined from high pressure mercury to product a high-pressure mercury injection curve; adjusting the $\sigma_{AM}\cos\theta_{AM}$ term until the high-pressure mercury injection curve closely matches the vapor desorption curve.

EXPERIMENTAL

Experiment 1

Several core samples from the Bossier tight gas sand play in the Mimms Creek Field located in Freestone Co., Texas were analyzed and the results are presented below.

Procedure:
1. Clean subject samples using cycles of a miscible solvent sequence to remove all hydrocarbons and aqueous pore fluids.
2. Dry to stable weight and determine basic sample properties.
3. Vacuum saturate sample with synthetic brine. The brine salinity is chosen so the precipitation will not occur during the vapor desorption process.
4. Pressurize pore volumes or back pressure flush to ensure 100% brine saturation.
5. Generate a low-pressure capillary pressure curve to a maximum of 1,000 psi using either porous plate or centrifuge methods.
6. Record the final sample weights at irreducible water saturation determined at test conditions (Swi).
7. Place samples into the electronically controlled humidity chamber at the $1^{st}$ (highest) relative humidity set point (approximately 90% RH)
8. Monitor sample weights daily until stable. Calculate average brine saturation for each sample based on the Swi weight minus the sample dry weight divided by the sample pore volume. Calculate brine salinity in each sample.
9. The capillary pressures are calculated using a modified Kelvin equation: Pc=ln(RH/100)RT/Vm.
10. Repeat steps 7 through 9 at the next lower oven RH setpoint (typically 80% RH).
11. Repeat steps 7 through 9 at the next lower oven RH setpoint (typically 70% RH).
12. Repeat steps 7 through 9 at the next lower oven RH setpoint (typically 60% RH).
13. Report vapor desorption based brine saturations vs capillary pressure for each sample.

Results:

TABLE 1

Capillary Pressure by Centrifuge Method

| Sample HB1-26 Satn. fract | Sample HB2-28 Satn. fract | Sample HB2-32 Satn. Fract | Sample HB3-17 Satn. Fract | Sample HB3-42 Satn. Fract | Sample HB4-18 Satn. fract | Approximate Average Capillary Pressure |
|---|---|---|---|---|---|---|
| 0.9110 | 0.9900 | 0.7410 | 0.4820 | 0.5370 | 0.6520 | 100 |
| 0.8500 | 0.9500 | 0.5710 | 0.3000 | 0.3800 | 0.6220 | 200 |
| 0.7450 | 0.8630 | 0.4390 | 0.1960 | 0.2690 | 0.5680 | 400 |
| 0.5260 | 0.7680 | 0.3110 | 0.1150 | 0.1700 | 0.4420 | 1000 |

TABLE 2

Capillary Pressure Using an Electronically Controlled Humidity Chamber to Collect Vapor Desorption Data

| | Sample No. HB1-26 | | | Sample No. HB2-28 | | | Sample No. HB2-32 | | |
|---|---|---|---|---|---|---|---|---|---|
| Relative Humidity, % | Weight, g | Satn, fract | Capillary Pressure, psi | Weight, g | Satn, fract | Capillary Pressure, psi | Weight, g | Satn. fract | Capillary Pressure, psi |
| 90% | 44.1300 | 0.3582 | 2217 | 68.6420 | 0.5812 | 2226 | 61.7240 | 0.2130 | 2218 |
| 80% | 43.9340 | 0.1499 | 4725 | 68.1790 | 0.2322 | 4738 | 61.4430 | 0.0837 | 4712 |
| 70% | 43.8670 | 0.0786 | 7593 | 68.0280 | 0.1183 | 7606 | 61.3530 | 0.0423 | 7550 |
| 60% | 43.8310 | 0.0404 | 10967 | 67.9450 | 0.0558 | 10915 | 61.3040 | 0.0198 | 10775 |

| | Sample No. HB3-17 | | | Sample No. HB3-42 | | | Sample No. HB4-18 | | | Average |
|---|---|---|---|---|---|---|---|---|---|---|
| Relative Humidity, % | Weight, g | Satn. fract | Capillary Pressure, psi | Weight, g | Satn. fract | Capillary Pressure, psi | Weight, g | Satn. fract | Capillary Pressure, psi | Capillary Pressures, psi |
| 90% | 62.2480 | 0.0605 | 2191 | 63.2970 | 0.0941 | 2197 | 57.3160 | 0.2841 | 2212 | 2210 |
| 80% | 62.0950 | 0.0209 | 4600 | 63.0770 | 0.0334 | 4625 | 56.8900 | 0.1066 | 4685 | 4681 |
| 70% | 62.0540 | 0.0103 | 7298 | 63.0150 | 0.0163 | 7344 | 56.7650 | 0.0546 | 7500 | 7482 |
| 60% | 62.0360 | 0.0057 | 10445 | 62.9860 | 0.0083 | 10422 | 56.7010 | 0.0279 | 10767 | 10715 |

FIG. 1 is a graphical presentation of the above capillary pressures using the average capillary pressures, wherein the capillary pressures up to 1,000 psi (Table 1) were determined using the centrifuge method and capillary pressures above 1,000 psi (Table 2) were determined using the method of the present invention. Although there is no direct overlap or connection between the vapor desorption data of the present invention and the centrifuge data, they do appear to follow a consistent trend, thus validating the vapor desorption measurements of the present invention. Also, although there is no direct overlap in the data, one can observe a very clear and obvious continuity in the composite capillary curves. It is shown that the two methods are in continuum at the capillary pressure range of 1000-2000 psi for the six samples tested. The merged data satisfactorily provide drainage curves that span the complete saturation range. This continuity provides confidence that the vapor desorption method provides an accurate description of the saturation distribution in the low water saturation and high capillary region of the capillary pressure curve.

The experiment also shows that core samples having both low water saturations and high capillary pressures can be produced in the laboratory using the vapor desorption method of the present invention.

Experiment 2

The electrical properties from a core sample from the Dowdy Ranch Field in Freestone Co., Texas were measured for varying capillary pressures.

TABLE 3

Sample 218
Rw, ohm-m @25° C.: 0.1237

| Water Saturation, Fraction pv | A/B Capillary Pressure, psi | Leverett J Function | Resistivity Index | | Incremental Saturation n |
|---|---|---|---|---|---|
| | | | Rt, ohm-m | R1 (Rt/Ro) | |
| 0.956 | 100 | 0.15 | 29.66 | 1.058 | −1.25 |
| 0.914 | 140 | 0.21 | 32.57 | 1.162 | −1.67 |
| 0.822 | 200 | 0.30 | 39.19 | 1.398 | −1.71 |
| 0.545 | 400 | 0.59 | 73.86 | 2.635 | −1.60 |
| 0.303 | 700 | 1.03 | 174.0 | 6.206 | −1.53 |
| 0.263 | 1000 | 1.48 | 207.0 | 7.384 | −1.50 |
| 0.142 | 2105 | 3.11 | 362.5 | 21.14 | −1.56 |
| 0.082 | 4506 | 6.65 | 690.1 | 60.47 | −1.64 |
| 0.046 | 7163 | 10.6 | 1429 | 161.5 | −1.65 |
| 0.035 | 10268 | 15.2 | 2321 | 251.0 | −1.65 |

Formation Factor FF(Ro/Rw) = 226.6
Ro, ohm-m = 28.03
Cementation Exponent, m = −2.01
Saturation Exponent, n = −1.57

In this experiment, the capillary pressures up to 1000 psi were determined using the centrifuge method while the capillary pressures above 1000 psi were determined by the method described herein using an electronically controlled humidity chamber with temperature controls.

Experiment 3

Several core samples from North Louisiana Field Well No. 1 were analyzed and the results are present below.

Procedure:

The core samples were prepared for testing in a fashion very similar to that in steps 1-4 of Experiment 1 above. The test sequence began by desaturating the core samples and measuring capillary pressures using the high speed centrifuge method. Capillary pressures were measured at four pressure steps: 100, 200, 400, and 1000 psi. For capillary pressures above 1000, the present inventive method, outlined in Experiment 1, was used to determine capillary pressures.

High-pressure, mercury injection capillary pressure (MICP) testing was the last set to be completed due to the destructive nature of this test. Drainage capillary pressure measurements were completed using a 117-pressure-step protocol—25 pressure steps in the low-pressure chamber (below atmospheric) and 92 pressure steps in the high-pressure chamber—corresponding to a measured capillary pressure range of 0 psig to 60000 psig. All mercury data were conformance corrected (low pressure end) for surface sample roughness, but were not blank corrected (high pressure end). Finally, the MICP were converted to an air-brine system at laboratory conditions for comparison to the combined data from the centrifuge method and vapor desorption method (according to the present invention).

Figure 2:
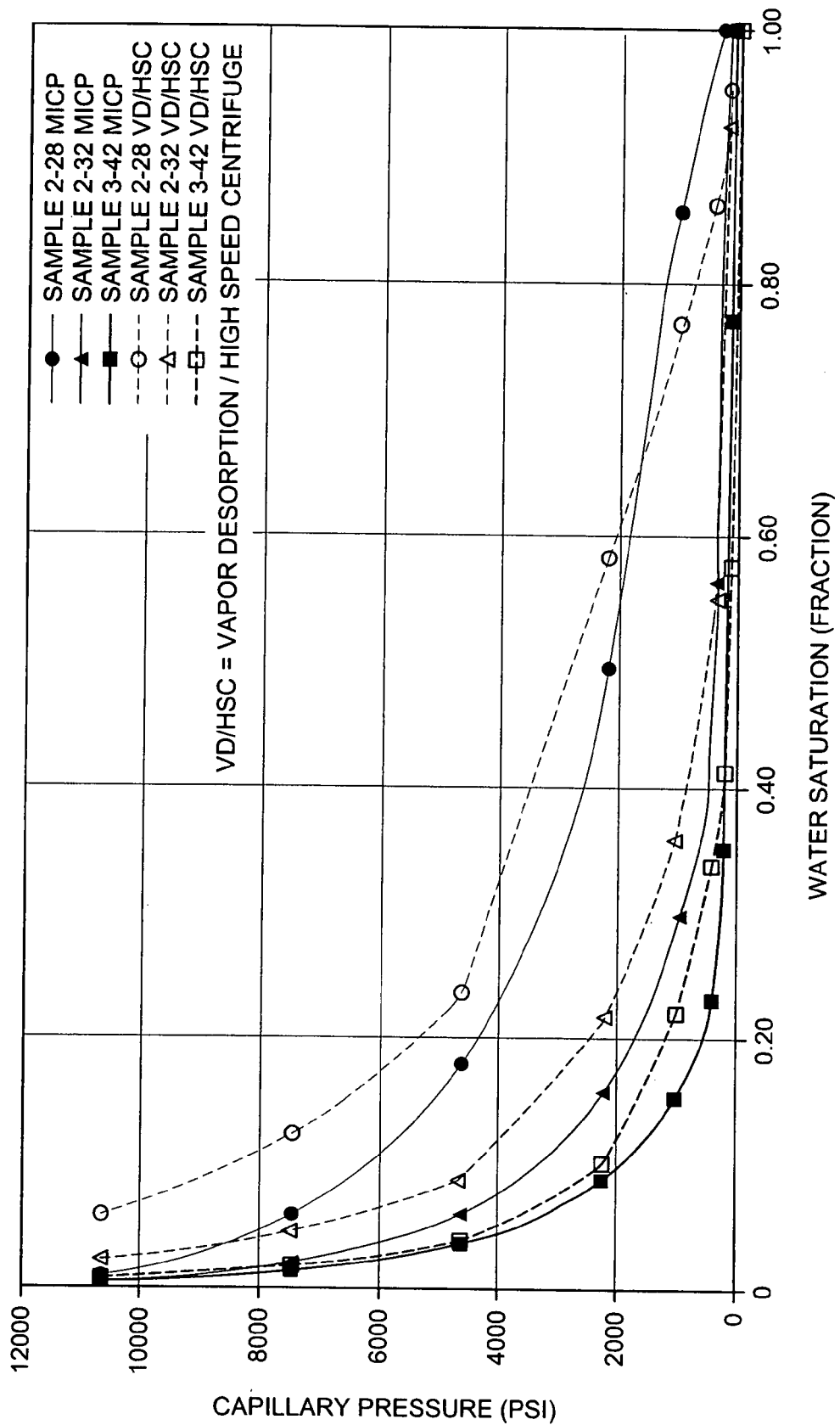
FIG. 2 is a graphical presentation of capillary pressures from Experiment 3 reported herein.

Results:

FIG. 2 shows the combined capillary pressures from high speed centrifuge data and vapor desorption data (obtained according to the present inventive method). FIG. 2 also shows the untransformed high-pressure mercury injection capillary pressures (MICP). As shown, the MICP curves not only exhibit higher capillary pressures, but also predict lower water saturations than the combined centrifuge and vapor desorption curves for a given capillary pressure.

Figure 3:
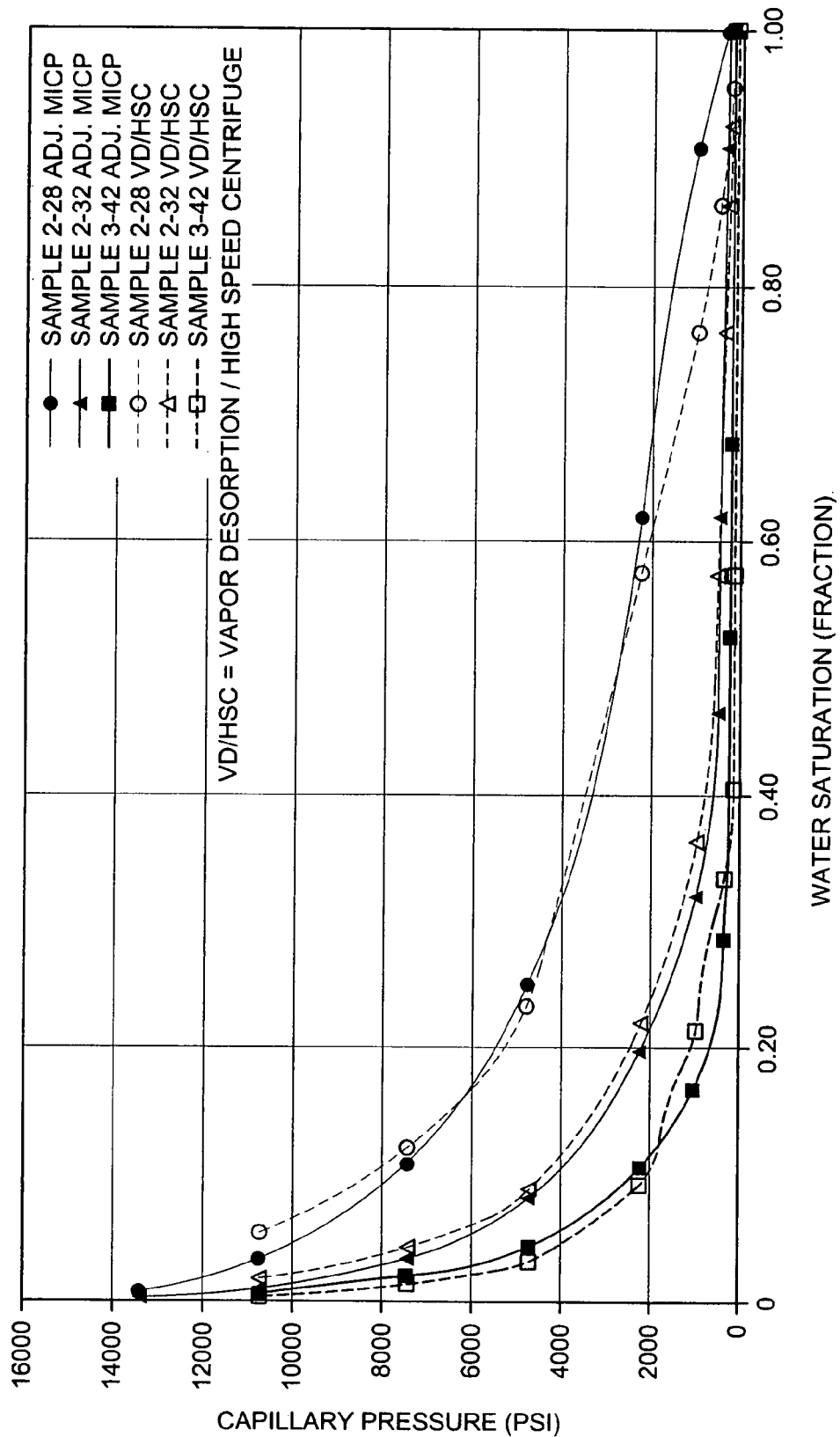
FIG. 3 is a graphical presentation of capillary pressures from Experiment 3 reported herein.

FIG. 3 shows the same combined centrifuge and vapor desorption capillary pressure curves as shown in FIG. 2. With regard to the high-pressure mercury injection capillary pressures, the mercury injection method uses an air-mercury system in which mercury displaces air during the injection process. Since this test is considered to be a drainage process (i.e., the wetting phase saturation is decreasing), then air must be regarded as the wetting phase. In fact, neither air nor mercury is a true rock wetting fluid under any condition. The present invention shows a method to transform the MICP curves using the combined centrifuge and vapor desorption data (obtained according to the present inventive method). The transform process of the present invention will not only allow the salvaging of existing or legacy MICP data, but will also provide more accurate MICP data to define the reservoir fluid saturation distribution. The basis of the transform is a conversion of the air-mercury data to air-brine data (representative of the reservoir) using the following equation:

$$P_{cAW} = P_{cAM}\left(\frac{2\sigma_{AW}\cos\theta_{AW}}{2\sigma_{AM}\cos\theta_{AM}}\right)$$

where:
  $P_{cAW}$=pseudo air-water capillary pressure, psi
  $P_{cAM}$=air-mercury capillary pressure, psi
  $\sigma_{AW}$=air-water surface tension
  $\sigma_{AM}$=air-mercury surface tension
  $\cos\theta_{AW}$=air-water contact angle
  $\cos\theta_{AM}$=air-mercury contact angle The MICP curves of FIG. 2 were transformed by decreasing the $\sigma_{AM}\cos\theta_{AM}$ term of the air-mercury system until the mercury curves closely matched the vapor desorption curves. As shown in FIG. 3, after transformation, the MICP curves closely match the combined centrifuge and vapor desorption curves.

The present inventive method is advantageous over known methods of determining high capillary pressures of a core sample because other methods, centrifuge and porous plate, can not reach high capillary pressure, and high pressure mercury injection, while it can reach high capillary pressure, is inaccurate especially at high capillary pressures. The vapor desorption method of the present invention provides an alternate method for extending capillary pressure measurements into the high capillary pressure and ultra-low water saturation range. The present invention provides for determining capillary pressures in excess of 10,000 psi air/brine yielding water saturations below 5%. The present inventive method is well suited for reservoir systems characterized by ultra-low water saturations and abnormally high capillary pressures such as tight gas sands.

Also, the present invention is advantageous because it provides a method for producing core samples having high capillary pressure and low water saturation which can then be tested concurrently for electrical properties. There is no known method for producing core samples having such high capillary pressures.

Further, the present invention is advantageous because it provides an accurate method of transforming capillary pressure data determined from high-pressure mercury injection which are generally known to be inaccurate especially at high capillary pressures.

All publications referred to herein are hereby incorporated by reference in their entireties.

Having described the invention above, various modifications of the techniques, procedures, materials, and equipment will be apparent to those skilled in the art. It is intended that all such variations within the scope and spirit of the invention be included within the scope of the appended claims.

What is claimed is:

1. A method for determining an electrical property of a core sample having a capillary pressure above about 4200 psi, comprising the steps:
   drying the core sample,
   weighing the core sample,
   saturating the core sample with a brine solution,
   weighing the core sample,
   calculating the brine volume,
   placing the core sample in an electronically controlled humidity chamber with temperature controls,
   setting a humidity level in the humidity chamber at about 80% or lower,
   periodically weighing the core sample to determine when equilibrium water saturation is achieved at the humidity level,
   calculating the capillary pressure at or above about 4200 psi, and
   measuring an electrical property of the core sample.

2. The method of claim 1, wherein the electrical property is formation factor, resistivity index, cementation exponent or saturation exponent.

* * * * *